US00PP08855P

United States Patent [19]

Fruehwirth

[11] Patent Number: Plant 8,855

[45] Date of Patent: Aug. 2, 1994

[54] POINSETTIA PLANT 'F-29'

[75] Inventor: Franz Fruehwirth, Encinitas, Calif.

[73] Assignee: Paul Ecke Ranch, Encinitas, Calif.

[21] Appl. No.: 163,475

[22] Filed: Dec. 7, 1993

[51] Int. Cl.[5] ..... A01H 5/00
[52] U.S. Cl. ..... Plt./86.3
[58] Field of Search ..... Plt. 86.3

*Primary Examiner*—James R. Feyrer

*Attorney, Agent, or Firm*—Arnold, White & Durkee

[57] ABSTRACT

Poinsettia 'F-29' is a new cultivar of the "curly" flower type, distinguished by peach pink bracts and unique flower bract formation and presentation. 'F-29' is a seedling from cross pollination. The new plant produces a very desirable flowering pot plant. The post-production foliage and bract retention is excellent even under low light intensities in the consumer's home.

1 Drawing Sheet

BACKGROUND OF THE NEW PLANT

This new poinsettia cultivar, 'F-29', originated as a seedling from cross pollination in my greenhouse in Encinitas, Calif., and was selected because of its unusual flower bract color, bract formation and bract presentation; traits which distinguish it from other poinsettia cultivars, and seem to make it a desirable plant for commercial greenhouse production. After selection, 'F-29' was vegetatively reproduced from stem cuttings for test purposes in Encinitas, Calif. By subjecting clones of this plant to successive generations of vegetative propagation, it was demonstrated that the distinctive characteristics of 'F-29' held true from generation to generation.

DESCRIPTION OF THE PHOTOGRAPHS

Poinsettia 'F-29' is illustrated in the accompanying color photographs.

The upper photo is a side view of 3 single stem plants per pot in full flower.

The lower photo is a top view of the same plants showing flower and bract formation.

DESCRIPTION OF THE PLANT

The following is a detailed description of this new poinsettia as observed in Encinitas, Calif., U.S.A. during December 1992. Observations were recorded from flowering plants, grown as 3 unpinched plants per pot. The pot was 14 cm in diameter and 11 cm in height. Color designations are compared to the 1986 edition of R.H.S. Colour Chart, first published in 1966 by The Royal Horticultural Society, London, England.

This new plant of the "curly" flower type is distinctly different than the poinsettia named 'Pink Curly' (U.S. Plant Pat. No. 4,950) in the following respects. The leaves of 'F-29' are green near RHS 147A, those of 'Pink Curly' are near RHS 137A. The stem stiffness of this invention is significantly improved over 'Pink Curly.' The bract color of 'F-29' is a peach pink near RHS 23D; the bract color of 'Pink Curly' is between RHS 51A and 52A.

THE PLANT

Origin: Seedling from cross pollination. Parents were seedlings of unknown lineage which are neither patented nor distributed to the public.

Classification:

*Botanic.*—*Euphorbia pulcherrima* Willd.

*Common name.*—Poinsettia.

*Cultivar name.*—'*F-29*'.

Form: Shrub.

Height: Short to Medium.

Growth habit: As a single stemmed plant, upright and sturdy. The application of a chemical growth retardant may not be needed to restrict height for commercial pot plant production. I observed 3 single stem plants per pot with an overall height of 42 cm and an overall width of 36 cm. The bract diameter of individual flowers was 18 cm.

Branching: 'F-29' is not a self-branching cultivar. However, if the terminal growing point is removed before flower induction, 4–5 axillary branches will develop at a uniform and fast rate, resulting in a very desirable branched flowering plant.

Growth rate: Rooting of stem cuttings occurs in 12–18 days under intermittent mist. The plant will flower in about eight weeks under continuous long night conditions and night temperatures of about 16°–18° C.

Foliage: The foliage is clean and uniformly green from bottom to top of the plant. The leaves are of medium size, leaf blades typically being 11–12 cm long and 10–11 cm wide with leaf petioles 2 cm long. The midrib is convoluted or curled with the upper surface of the leaf being the outer surface of the curve. The unique appearance of the leaves may be described as puckered and arched as might be caused by pulling a drawstring inside the midrib.

*Leaf shape.*—Typical leaves are generally ovate with obtuse bases and acuminate tips. Leaf margins are notched and lobed usually with 1 major lobe on earth side of the leaf blade.

*Color.*—Upper side — Green, near RHS 147A. Under side — Green, near RHS 147B.

*Retention.*—The foliage lasts extremely well even under low light intensities in the consumer's home.

Bracts: Generally there are 18–21 peach pink bracts of various sizes subtending the cyathia. The bract surface is rugose with the midrib convoluted or curled. Together, the convexity of the bracts make a coarsely convoluted, spherical flower head. The primary bracts have blades typically 11–12 cm long and 9–10 cm wide with petioles about 2 cm long.

*Shape.*—Primary bracts are mostly ovate with acute to obtuse bases and acuminate tips. Primary bracts are lobed usually with 1 indentation on either side of the bract. Secondary bracts are ovate to elliptic and have entire margins.

*Color.*—Upper side — The larger transitional and primary bracts are peach pink near RHS 23D. The secondary bracts have the same peach pink base color, but overlain with a pink blush near RHS 48D. Under side — Peach pink. The color of the primary bracts is near RHS 23D. The pattern of the pink blush mirrors the upper surface. The color of the blush is near 48D.

Flowers: Generally, 19–22 cyathia (flowers) are present when the plant is in full bloom. Each cyathium is about 7 mm long and 6 mm wide, green in color, and with a creamy white fringe at the distal end. Usually one, but occasionally two yellow nectar cups protrude from the side of each cyathium and secrete nectar. The flower pedicel is also green and about 5 mm in length. The stamens protruding from the cyathia are white. The anthers are bifurcate; the pollen is yellow. The stigmas are trifurcate and red.

*Nectar exudate.*—Abundant.

*Seeds.*—Self-incompatible.

*Fertility.*—Not observed.

Post production: The leaf, cyathium and bract retention is excellent and the bracts do not fade or discolor.

What is claimed is:

1. A new and distinct Poinsettia cultivar, substantially as herein shown and described, distinguished by its unique peach pink flower bracts and unusual bract formation and presentation.

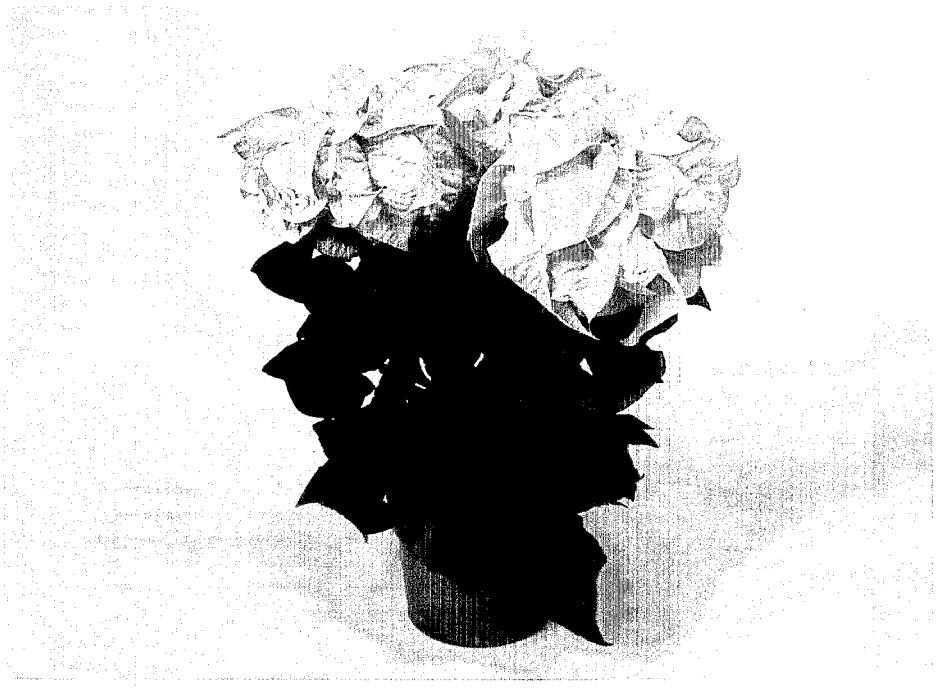
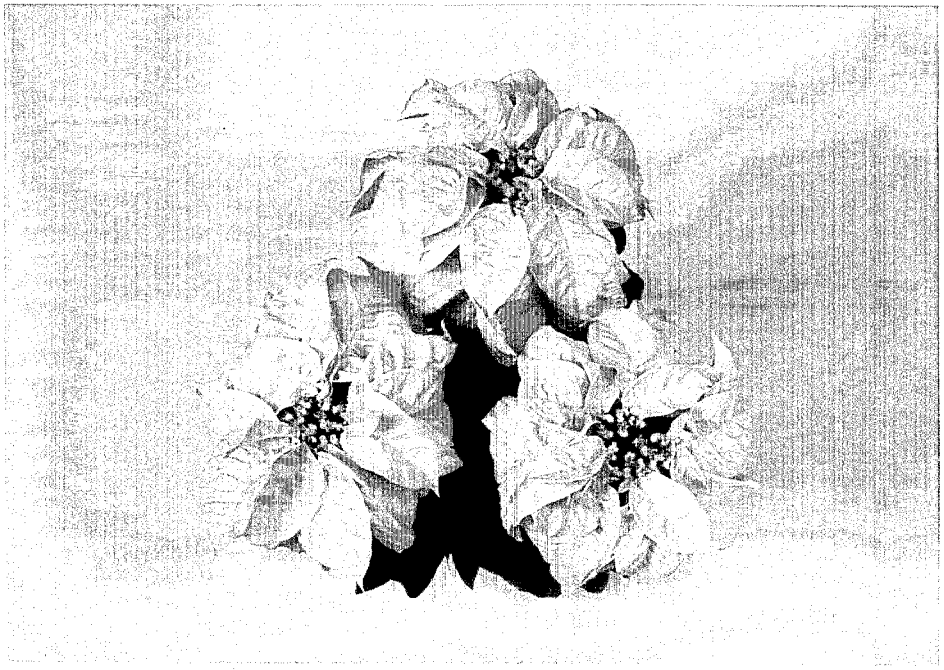

* * * * *